(12) United States Patent
Matsunaga et al.

(10) Patent No.: US 7,405,042 B2
(45) Date of Patent: Jul. 29, 2008

(54) METHOD OF EXTRACTING NUCLEIC ACID OR PROTEIN USING DENDRIMERS AND DENDRIMER-COMPOSITIONAL SUBSTANCES

(75) Inventors: Tadashi Matsunaga, Koganei (JP); Haruko Takeyama, Koganei (JP); Brandon Yoza, Koganei (JP); Kazuhisa Fukushima, Musashino (JP); Saya Satou, Musashino (JP)

(73) Assignee: Yokogawa Electric Corporation, Musashino-shi, Tokyo (JP)

( * ) Notice: Subject to any disclaimer, the term of this patent is extended or adjusted under 35 U.S.C. 154(b) by 654 days.

(21) Appl. No.: 10/647,232

(22) Filed: Aug. 26, 2003

(65) Prior Publication Data

US 2005/0260600 A1 Nov. 24, 2005

(30) Foreign Application Priority Data

Sep. 17, 2002 (JP) .............................. 2002-269867

(51) Int. Cl.
*C12Q 1/68* (2006.01)
*G01N 33/53* (2006.01)
*A61K 9/14* (2006.01)
*A01N 25/00* (2006.01)

(52) U.S. Cl. ............................. 435/6; 435/7.1; 435/7.2; 424/486; 514/772

(58) Field of Classification Search ...................... 435/6, 435/7.1, 7.2; 424/486; 514/772
See application file for complete search history.

(56) References Cited

U.S. PATENT DOCUMENTS

2002/0006626 A1* 1/2002 Kim et al. ..................... 435/7.1
2005/0287560 A1* 12/2005 Garimella et al. ............... 435/6

FOREIGN PATENT DOCUMENTS

| JP | 8-176212 | 7/1996 |
| JP | 11-313670 | 11/1999 |

OTHER PUBLICATIONS

Partial English translation of "DNA Chips and It's Application", Detection of Genes Using Beads, CMC Co., Ltd., Jul. 2000. Discussed in the specification.

* cited by examiner

*Primary Examiner*—Jezia Riley
(74) *Attorney, Agent, or Firm*—Westerman, Hattori, Daniels & Adrian, LLP.

(57) ABSTRACT

The present invention relates to a method of extracting nucleic acid or protein, in which multi-layer dendrimers are formed on the surface of fine particles, amino radicals for capturing nucleic acid or protein are formed on the surface of these dendrimers, and nucleic acid or protein is extracted using these amino radicals. The present invention can greatly and easily increase the recovery ratio of nucleic acid or protein.

29 Claims, 4 Drawing Sheets

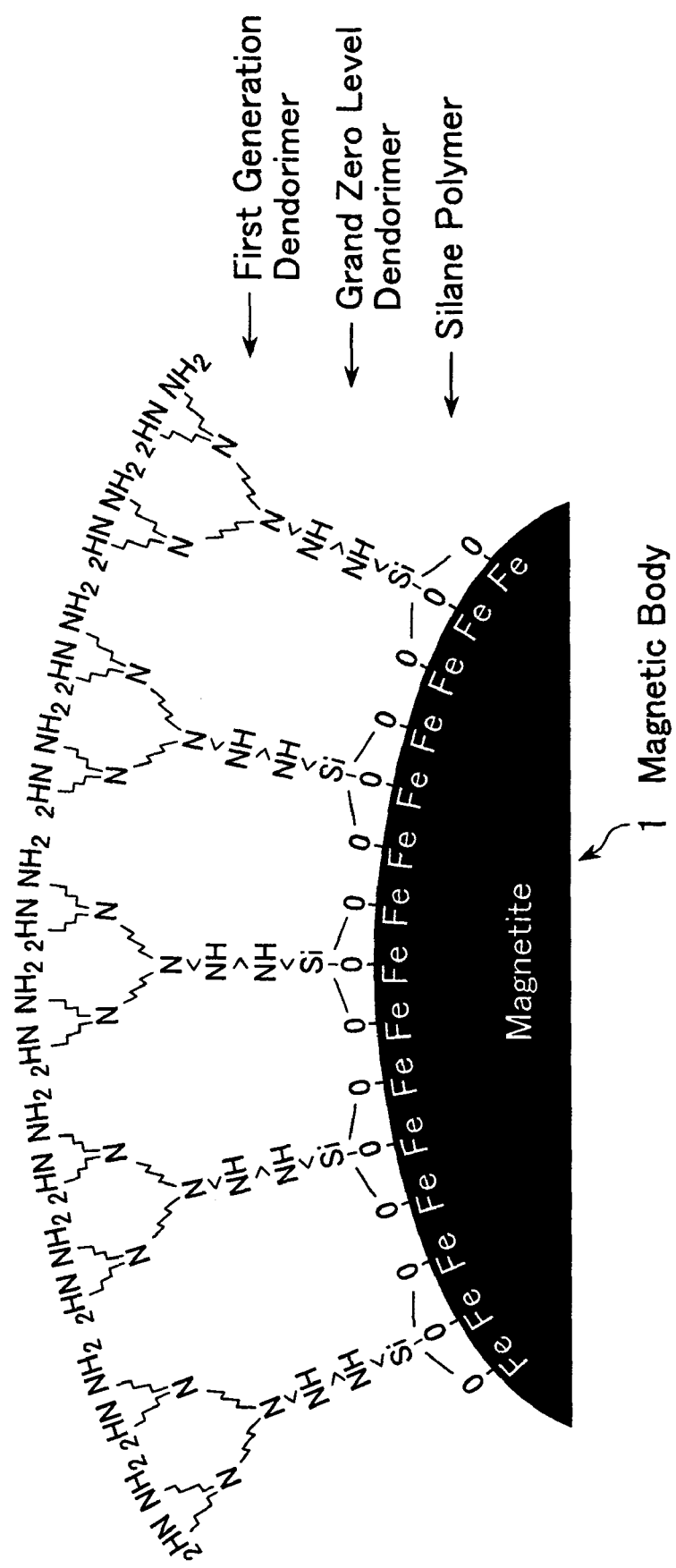

SEQUENCE LISTING

```
<160> NUMBER OF SEQ ID NOS: 4

<210> SEQ ID NO 1
<211> LENGTH: 30
<212> TYPE: DNA
```

```
<213> ORGANISM: artificial
<220> FEATURE:
<223> OTHER INFORMATION: primer

<400> SEQUENCE: 1
gggatgcata tggaagacgc caaaaacata                                    30

<210> SEQ ID NO 2
<211> LENGTH: 33
<212> TYPE: DNA
<213> ORGANISM: artificial
<220> FEATURE:
<223> OTHER INFORMATION: primer

<400> SEQUENCE: 2
gggatgcata cttgattaca atttggactt tcc                                33

<210> SEQ ID NO 3
<211> LENGTH: 15
<212> TYPE: DNA
<213> ORGANISM: artificial
<220> FEATURE:
<223> OTHER INFORMATION: primer

<400> SEQUENCE: 3
ggcctcccac accag                                                    15

<210> SEQ ID NO 4
<211> LENGTH: 23
<212> TYPE: DNA
<213> ORGANISM: artificial
<220> FEATURE:
<223> OTHER INFORMATION: primer

<400> SEQUENCE: 4
gcgggcaggc gtcagcacca gta                                           23
```

METHOD OF EXTRACTING NUCLEIC ACID OR PROTEIN USING DENDRIMERS AND DENDRIMER-COMPOSITIONAL SUBSTANCES

BACKGROUND OF THE INVENTION

1. Field of the Invention

The present invention relates to a method of extracting nucleic acid or protein, and more precisely, to a method of extracting nucleic acid or protein by dendrimers using fine particles and dendrimer-compositional substances.

2. Description of the Prior Art

In recent years, automation of DNA extraction has been strongly desired in the fields of medical service and experiments. Commercially-available pre-treatment systems for extracting nucleic acid and protein can be roughly divided into magnetic beads systems and centrifugal separation systems.

A magnetic beads system, for example, is described in "3. Detection of Genes Using Beads" in Section 7 of "DNA Chip Application Technologies," (published in July, 2000, by CMC Co. Ltd.). In addition, these systems are not limited to those using magnetic beads, but also include those using magnetic particles (for magnetic particles, for example, refer to the gazette of Japanese Laid-open Patent Application No. 8-176212) and those using magnetic bodies (for magnetic bodies, for example, refer to the gazette of Japanese Laid-open Patent Application 11-313670).

These magnetic beads systems are smaller in size and more easy to handle compared with the centrifugal separation systems. However, the magnetic beads systems have a problem that they have a rather small rate of capturing nucleic acids or proteins and thus do not necessarily provide satisfactory yields because projected structures for capturing nucleic acids or proteins formed on the surfaces of magnetic beads are sparse.

SUMMARY OF THE INVENTION

The object of the present invention is to solve the above-described problem, that is, to achieve a nucleic acid or protein-extracting method using dendrimers, which can greatly increase the recovery ratio of nucleic acids or proteins by building dendrimers containing fine particles and covering the dendrimers with amino terminal radicals for capturing nucleic acids or proteins, and to realize dendrimer-compositional substances.

BRIEF DESCRIPTION OF THE DRAWINGS

FIG. 1 is a conceptual configuration drawing for dendrimers in the present invention.

FIG. 3 is a drawing indicating the results of electrophoresis for DNA.

DETAILED DESCRIPTION OF THE PREFERRED EMBODIMENTS

Figure 2A:
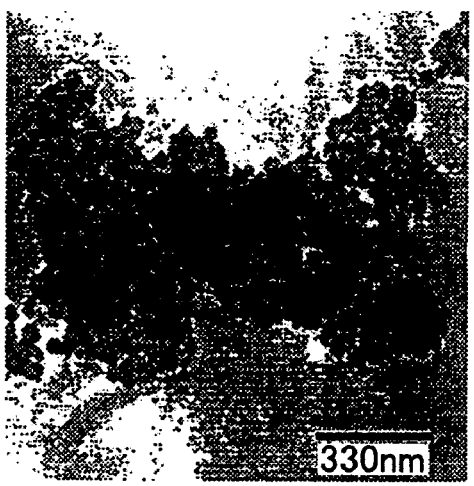
FIG. 2 shows electron-microscope photographs of bacteria-derived magnetic bodies.

The present invention relates to a method for efficiently extracting nucleic acid or protein (hereinafter DNA is used as an example) from fluid samples by synthesizing multi-branched modification using polyamide-amine dendrimers on the surface of fine particles, and to dendrimer-compositional substances.

In addition, as fine particles in the present invention, fine particles of bacteria-derived magnetic bodies, artificial magnetic bodies, metals, plastic beads, glass beads, gel-state materials, etc. can be used. However, for this embodiment, the description will refer to a bacteria-derived magnetic body, one of the examples of the fine particle, as an example to simplify the description.

The use of a solid-phase magnetic body is a very effective means of extracting DNA from cytoplasmic admixtures. The method of extraction using magnetic bodies can shorten the extracting time, consumes a smaller quantity of reagents used, and is easy to automate the process of separation, when compared with conventional methods. If bacteria-derived magnetic bodies are used as magnetic bodies, each magnetic body consists of a single-phase iron dioxide of size 50 to 60 nm and this is a size suitable for extracting DNA.

The present invention and an embodiment of the present invention will now be described in detail using the drawings. In the present invention, multi-branched polyamide-amine dendrimers are obtained by implementing silanization on the surface of fine particles, such as bio-derived magnetic bodies, using a sililation reagent or a silane-coupling reagent and laminating amide-amine formed by the reaction of methyl acrylate and ethylenediamine on the above silanization as dendro-units.

(1) FIG. 1 is a conceptual configuration drawing for dendrimers formed by such a method. As magnetic body 1, for instance, a bacteria-derived magnetic body is used. The bacteria-derived magnetic body can be obtained, after breaking bacteria plasma membrane by applying pressure to them, by recovering them using a magnet and applying suitable treatment to them.

More specifically, collected bacteria cells are broken in five steps with 1100 kg/cm$^2$. After applying a uniform magnetic field (the surface magnetic field is 0.37 T) to broken cells, the magnetic bodies are taken out using an Nd—B magnet (10 mm×10 mm×6 mm). Collected magnetic bodies are subjected to disinfection by means of ultrasonic washing three times and then stored in buffer solution at 4° C.

The magnetic body concentration is determined by the weight in the dry condition. The magnetic bodies are diffused using ultrasonic waves and are dispensed by every 0.5 mL in 5 mL tubes whose weights have been measured after being dried for 4 hours at 180° C. in advance. Each of the dispensed magnetic bodies is washed two or more times in an ultrasonic wave chamber using a solution of 1:1:1 concentration of chloroform, methanol, and hexane.

The magnetic bodies are separated from the solution using magnetism to remove solvent. Collected magnetic bodies are dried for four hours at 180° C. after removing residual solvent using vacuum drying for 15 minutes.

(2) The bacteria-derived magnetic bodies obtained as described above are subjected to silanic modification on their surfaces. The magnetic body solution is dispensed so that a concentration of 100 mg/mL is obtained as a whole, then magnetic bodies are recovered with an Nd—B magnet and the solution is removed. The magnetic bodies are separated using magnetism and the solvent is removed. Collected bacteria-derived magnetic bodies are dried for 15 minutes in vacuum and are suspended in 99% ethanol whose volume is the same as that of the original solution after removing residual solvent.

Amino-silane polymers (called AEEA) are subjected to hydrolysis using 1 mM acetic acid 1% solution in 99% ethanol, then directly covalently bonded to the surface of bio-derived magnetic bodies. Further, the magnetic bodies, after being lightly diffused in an ultrasonic wave chamber, are washed with 20 mL methanol three times and again suspended in the solution making them have the same volume as the original one.

(3) Next, multi-branched polyamide-amine dendrimers are laminated on the surface of the magnetic bodies subjected to amino-silane treatment as described above.

Dendrimer synthesis is started at the AEEA-coated 50 mg bacteria-derived magnetic bodies (in addition, the synthesis has also been started at the 50 mg artificial magnetic bodies in 20 mL methyl acrylate for the purpose of comparison).

In order to disperse the suspended state, an Erlenmeyer flask is dipped in the water in an ultrasonic wave chamber for three hours at 25° C. using a completely closed rotary evaporator.

The magnetic bodies are collected and washed with methanol. After washing, they are reacted in the 4 mL methanol and ethylenediamine 1:1 solution and the generated amide-amine is polymerized as a dendro-unit. The synthesis is proceeded while maintaining the same state thereafter.

Polymerization is proceeded by means of repeated reaction of methyl acrylate and ethylenediamine up to a target generation (FIG. 1 shows up to the second layer).

Then, the magnetic bodies are washed three times using 25 mL methanol, and next washed with 25 mL water. In this case, they are collected using magnetism between one washing stage and the next washing stage.

(4) Next, the surface amine is determined.

Modified magnetic body 1 (250 μg) is dipped in 200 μL 10 mM sulfosuccinimidyl 6-[3'(2-pyridyldithio)-propioneamide]hexanoate (sulfo-LC-SPDP) solution for 30 minutes and are subjected to growth and extension. Treated magnetic bodies are washed with distilled water three times and are collected using magnetism.

The magnetic bodies and sulfo-LC-SPDP polymers are subjected to growth-reaction in 200 μL 20 mM dithiothreitol, and then also quantitatively measured using a spectroscope at a wavelength of 343 nm. Data are compared with unmodified magnetic bodies for performance and the concentration is determined based on a standard curve obtained using 5 mM sulfo-LC-SPDP and 20 mM dithiothreitol.

When the magnetic bodies modified as described above (AEEA 200 μg-modified third-generation dendrimers and AEEA 100 μg-modified fifth- and sixth-generation dendrimers) are mixed with 25 μg of calf thymus DNA, handled to obtain 1 mL in 20 mM tris-hydrochloric acid buffer solution (Tris-HCl) (pH 7.0), turned upside down, then subjected to a 6000 rpm micro centrifuge, the following results are obtained:

Absorbance of the supernatant liquid is observed at 260 nm and the concentration of DNA is calculated using the standard curve to calf thymus DNA. The DNA can be exfoliated from magnetic bodies by being heavily stirred in 1 mL 2 M NaCl. Existence of DNA can be checked using electrophoresis of agarose gel after implementing ethanol-precipitation.

In addition, the present invention can be applied to extraction of 4.8 kbp pGEM-T plasmid containing luciferase genes.

Further, DNA extraction from *Escherichia coli* and the whole blood for direct PCR analysis has also been tried. *Escherichia coli* in which luciferase luminous enzyme is inserted into pGEM-T plasmid, are cultured until the cell concentration reaches $10^6$/mL in the culture solution containing 50 μg ampicillin. The cells are isolated using centrifugal separation.

Cells are dissolved by being dipped in 10% Triton-X solvent containing 75 μg protenase K for 30 minutes at 50° C. Bacteria-derived magnetic bodies grown to the sixth-generation 100 μg are added to the dissolved substances and the tube is quickly stirred. Magnetic bodies are collected using magnetism and the supernatant liquid is removed.

The magnetic bodies are washed six times using 20 mM Tris-HCl (pH 7.0) and the tube is shaken vertically every time and suspended substances are collected using magnetism. DNA is stirred sufficiently in 1 mL 2 M NaCl and exfoliated from magnetic bodies. The magnetic bodies are subjected to 6000 rpm centrifugal separation with a micro centrifuge.

Exfoliated DNA is measured with an absorption spectrophotometer and compared with the standard calibration curve for 2 M NaCl. A ratio of 260:280 is determined with the spectrophotometer. On the other hand, for a lot to which the same extraction has been done, DNA is not exfoliated from the magnetic bodies but suspended in 100 μL distilled water (Mill-Q water) without treatment to be used for PCR amplification. This lot is diluted with Mill-Q water while applying ultrasonic waves to the magnetic bodies and plasmid is PCR-amplified.

As the forward primer,

```
5'GGGATGCATATGGAAGACGCCAAAAACATA3'
(SEQ ID NO:1)
``` is used, and as the backward primer,

```
5'GGGATGCATACTTGATTACAATTTGGACTTTCC3'
(SEQ ID NO:2)
``` is used. In such a condition, 1.65 kbp luciferase genes found in plasmid are amplified.

The PCR products can be visualized by gel electrophoresis. DNA extracted from 1 μL human whole blood is also analyzed following the similar procedure using PCR. New samples are used and the anti-coagulative agent is not used.

As the forward primer used for PCR in the whole blood,

```
5'GGCCTCCCACACCAG3'
(SEQ ID NO:3)
``` is used, while as the backward primer,

```
5'GCGGGCAGGCGTCAGCACCAGTA3'
(SEQ ID NO:4)
``` is used.

The above-described points are summarized below.

The number of amines on the surface of the bacteria-derived magnetic bodies increases as the number of dendrimer layers increases from 1 to 6. As shown in FIG. 1, it is theoretically shown that the number of amines is doubled every time the number of generations increases from the start-line amino-silane layer.

TABLE 1

| Generation | Number of amines/BMP | Ratio of increase |
| --- | --- | --- |
| AEEA | $2.1 \times 10^4$ | |
| First generation | $6.8 \times 10^4$ | 350 |
| Third generation | $2.6 \times 10^5$ | 370 |
| Fifth generation | $1.1 \times 10^6$ | 420 |
| Sixth generation | $1.7 \times 10^6$ | 150 |

Figure 2B:
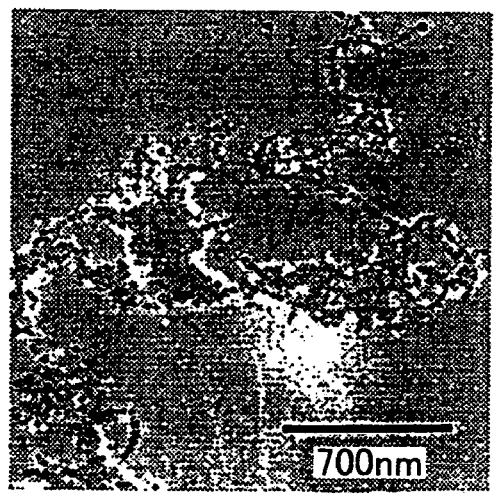
Figure 2C:
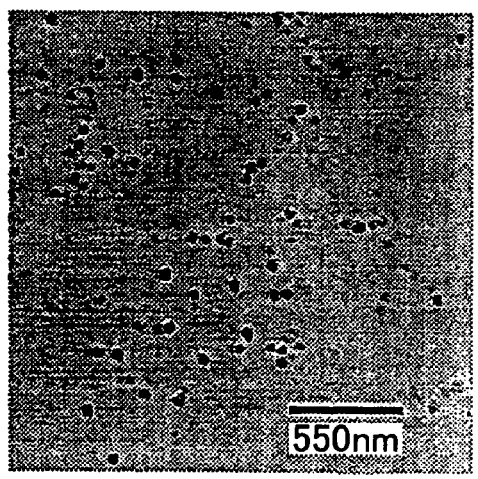
Figure 2D:
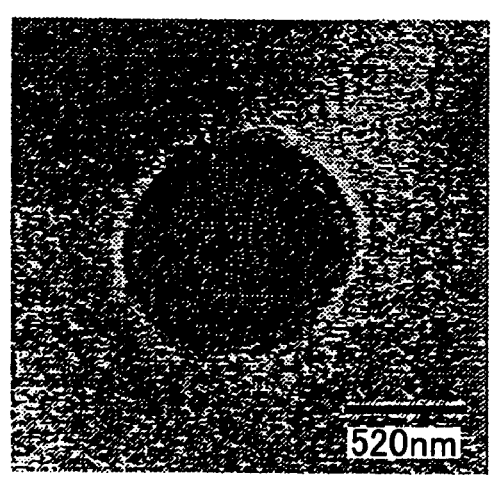

Table 1 indicates the number of amines of bacteria-derived magnetic bodies (BMP) in each generation. As shown in Table 1, the fact that amines double in number in each layer means that dendrimers maintain an ideal cascade construction. The surface area of one bacteria-derived magnetic body, if it is assumed to be a rectangular solid of 50×50×100 (nm), is $2.5 \times 10^4$ nm$^2$. On the surface of the sixth-generation layer, since the number of amines is $1.7 \times 10^6$, the numeric value of 68 amines/nm$^2$ is obtained. FIG. 2 shows photographs for modified and unmodified bacteria-derived magnetic bodies taken with an electron microscope. As shown in FIG. 2(a), unmodified magnetic bodies have mutual weak repulsive forces and it can be seen that they coagulate. Dendrimers of the third generation run in a chaining manner as shown in FIG. 2(b) and coagulate partly. Dendrimers of the sixth generation are obviously dispersed as seen in FIG. 2(c). And as shown in FIG. 2(d), a layer of about 4 nm covering the surface of the magnetic bodies is observed.

Extreme deterioration is not recognized for dendrimer-modified bacteria-derived magnetic bodies even after ultrasonic waves are applied. They are very well diffused without making large coagulation and, even if ultrasonic waves are not applied, they are sufficiently well diffused and suspended.

On the other hand, for artificial magnetic bodies, it is confirmed that they become easy to crush gradually as the number of generations increases when ultrasonic waves are applied. Table 2 shows the sizes and distribution of formed magnetic bodies.

If artificial magnetic bodies are dendrimer-extended up to the sixth generation, a large amount of about 14 nm fragments is diffused in the solution. Further, owing to the size being decreased and the structure becoming incomplete, coagulation is greatly decreased and paramagnetic fragments are generated.

TABLE 2

| | Distribution (%) (>125 nm) | Distribution (%) (50-125 nm) | Distribution (%) (<50 nm) |
| --- | --- | --- | --- |
| Bacteria magnetic bodies Without covering | 6 | 94 | 0 |
| Bacteria magnetic bodies The sixth generation | 1 | 99 | 0 |
| Artificial magnetic bodies Unmodified | 18 | 82 | 0 |
| Artificial magnetic bodies First generation | 0 | 34 | 66 |
| Artificial magnetic bodies Third generation | 0 | 17 | 82 |
| Artificial magnetic bodies Sixth generation | 0 | 0 | 100 |

If dendrimers are continually grown on bacteria-derived magnetic bodies, it is found that the magnetic bodies are capable of capturing DNA efficiently as shown in Table 3. In this case, modified magnetic bodies are mixed with 25 μg calf thymus DNA. Magnetic bodies on which dendrimers are extended up to the sixth generation are mixed with excess concentration DNA (50 μg).

The amount of capturing DNA increases as the dendrimer layer increases at dendrimer-modified magnetic bodies and in the sixth generation, 24.83±1.61 μg of DNA can be captured per 100 μg of magnetic bodies.

TABLE 3

| Generation | DNA per 100 μg of magnetic bodies (μg) |
| --- | --- |
| AEEA | 3.59 ± 0.37 |
| First generation | 4.43 ± 0.26 |
| Third generation | 5.89 ± 0.07 |
| Fifth generation | 11.95 ± 0.68 |
| Sixth generation | 24.83 ± 1.61 |

For the artificial magnetic bodies, the amount recovered by the AEEA layer shows no change with the amount of DNA captured by the dendrimer-extended layer. This is considered to be due to deterioration such as cracks, crushing, etc. in the magnetic bodies caused by ultrasonic waves.

At bacteria-derived magnetic bodies which are dendrimer-modified up to the sixth generation, DNA recovery is not sufficient if only 2 M NaCl is added resulting in only 24% recovery (refer to Table 4). The recovery ratio increases up to 87% (21.7±1.59 μg) by maintaining DNA polymers for 30 minutes at 50° C. in a thermostatic oven to increase the recovery ratio.

TABLE 4

| DNA | Conditions | DNA (μg)/100 μg | Recovery ratio |
| --- | --- | --- | --- |
| Calf thymus | 30° C., 10 min. | 6.07 ± 1.01 | 24% |
| Plasmid | 50° C., 30 min. | 21.70 ± 1.59 | 87% |
| Plasmid digests | 50° C., 30 min. | 19.22 ± 1.61 | 81% |

The capturing capability of small plasmid DNA is also investigated. Two kinds of products of about 3 kbp and 1.6 kbp are formed by extracting plasmid pGEM-T containing luciferase genes. The amounts of capture and recovery of plasmid DNA are 23.80±3.01 μg and 19.22±1.61 μg respectively. After examining these results using gel electrophoresis, no discrepancy based on the difference of sizes is recognized. As shown in FIG. 3(a), recovered DNA corresponds with the DNA recovered using magnetism in advance.

The amount of DNA extracted from *Escherichia coli* is measured after it is recovered by exfoliation from the magnetic bodies using 2 M NaCl. As a result of measurement of recovered DNA after treatment with ribonuclease (RNase), 30.25±7.74 μg of DNA was recovered per 100 μg of the sixth generation dendrimer-modified magnetic bodies.

The ratio of 260:280 (nm) is 0.93, showing that mixing of some protein occurs. The result of the previously-mentioned gel electrophoresis also shows that some degree of RNA contamination occurs.

As the result, after cytolysis, 3 μL RNase was added and when the DNA was measured after incubation for 20 minutes at 37° C., the recovery ratio of DNA decreased to 22.35±1.76 μg. PCR was implemented for the sample at a dilution ratio of 10 to 100-fold directly without lysis treatment of composite substance composed of magnetic bodies and DNA using a salt or RNase [refer to FIG. 3(b)].

In a similar manner, for DNA extracted from human whole blood, PCR could be directly implemented at a dilution ratio of 10 to 100-fold by the same process.

Based on the above results, the following conclusions can be obtained:

It is widely known that dendrimer modification can be extended in a stratified manner by the fact that amino-silane makes covalent bonding to bacteria-derived magnetic bodies as a polymerization initiator, and that stable cross-linking can be formed on bacteria-derived magnetic bodies obtained from magnetic bacteria AMB-1 using the conjugated bonding of amino-silane.

It is sufficient to examine the number of amine radicals on the surface of magnetic bodies for judging whether dendrimers are successfully formed on the bacteria-derived magnetic bodies. It is recognized that the number of amine radicals on the surface is linearly doubled in every generation up to the sixth generation. However, after the sixth generation, the number of amine radicals could not be accurately counted.

This is because large cyclic sulfo-LC-SPDP hexamer seems to cause steric-hindrance. In addition, it has been known previously that, as the generation increases, the time required for incubation must be taken longer following the increase.

That is, it has been considered that molecules must be grown by allowing sufficient time to avoid steric hindrance in the growth of molecules. In order to extend to the sixth generation from the fifth generation, the incubation time has to be extended up to six hours until it is acknowledged that amine radicals do not increase further even if reagents are added more.

Figure 4:
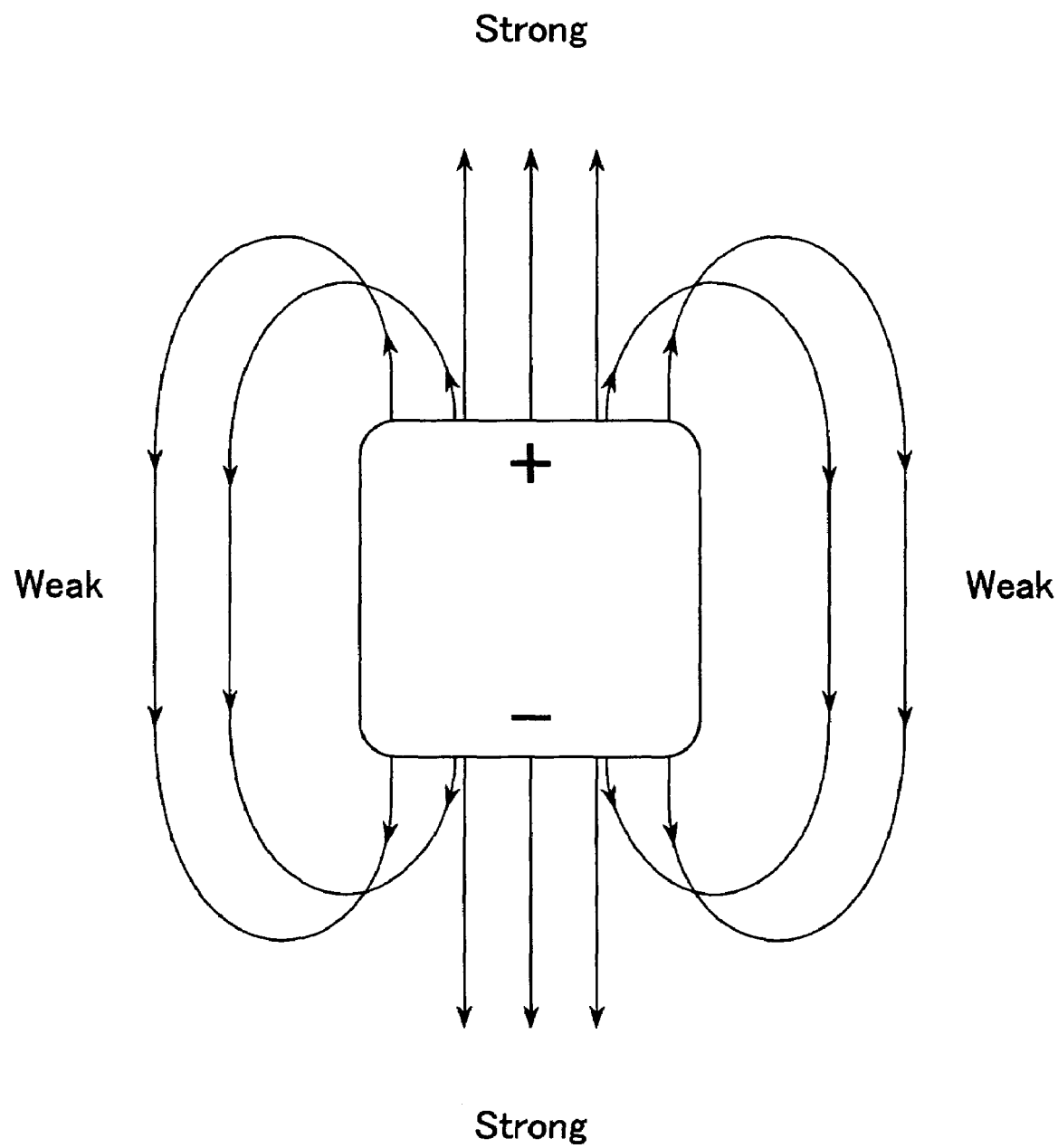
FIG. 4 is a drawing illustrating the magnetic field of a bacteria-derived magnetic body.

Accordingly, although further repetition of generation may be possible over the sixth generation, it cannot be easily determined physically. In addition, deducing from TEM (transmission electron microscope) images, the inter-ion repulsive force increases as the generation increases. Bacteria-derived magnetic bodies coagulate tightly only in the first generation. If there are generations up to the third generation, bacteria-derived magnetic bodies run like a row in a chaining manner. This phenomenon is also suggested by the fact that the strength of magnetic forces is proportional to the magnetic flux density in the direction of magnetic poles as shown in FIG. 4.

The existence of ion repulsive force tends to suppress the polar alignment of magnetic bodies. This is the same in the case where bacteria-derived magnetic bodies are covered with bio-membrane. That is, the repulsive force of the sixth-generation dendrimers is very large, exceeds the magnetic force and thus the magnetic bodies do not coagulate but are actually individually suspended.

Although synthesis of magnetic bodies artificially is possible, their dynamic characteristics and chemical behavior as physical properties are not definite because their shapes are not equal, crystallization is not sufficient, and their structure is not uniform. If dendrimers of the same size as bacteria-derived magnetic bodies are formed using artificial magnetic bodies, the artificial magnetic body polymers may cause coagulation and crushing and the increase of amine radicals on the surface may not become linear.

Since bio-derived magnetic bodies are crystallized, they do not suffer a loss even in the dendrimer forming process and maintain the original shapes and magnetism.

The dendrimer-modified bio-derived magnetic bodies greatly increase the recovery ratio of DNA compared with unmodified magnetic bodies. DNA is condensed in a regular structure of strong silane cations covering the surface of magnetic bodies and becomes a similar form to dendrimers through interactions with dendrimers. Positive ions, which are increased due to dendrimer-modified bio-derived magnetic bodies, greatly serve to increase the force to capture DNA which is charged negatively. This is also known by the fact that the addition of positive ion reagent increases DNA concentration.

However, the addition of positive ion reagent may cause unnecessary contamination. If dendrimer-modified bio-derived magnetic bodies are used, the DNA recovery ratio can be raised without adding positive ion reagent. Further, as is well known, the degree of dispersion and composite concentration in solution can be controlled by adjusting the number of amino radicals on the surface.

The use of magnetic bodies as seen in the present invention is superior to conventional methods in respect of treatment time, amount of reagent to be used, separation and recovery, and ease of automation. The process is very simple, only requiring a dissolving process before the washing process. In addition, if there is a limitation that PCR must be performed from a small amount of sample, this is the most suitable method for extracting sufficient DNA from a small amount of sample. This method is also applicable to designing a more compact system.

Furthermore, the present invention is not restricted to the above embodiment but may be embodied in other specific forms, changes, and versions without departing from the spirit or essential characteristics thereof.

For example, it is also possible to bond antibodies to the dendrimer surfaces and extract proteins using the antigen-antibody reaction.

As described above, the present invention has the following effects:

(1) By multi-branching dendrimers on the surface of bio-derived fine particles and covering them with amino terminal radicals, the ratio of extraction of nucleic acids or proteins can be easily increased.

(2) The use of dendrimers containing fine particles is superior to conventional methods of using magnetic beads in respect of treatment time, amount of reagent to be used, separation and recovery, and ease of automation.

(3) Although strong ultrasonic waves must be applied to dendrimers for sufficient diffusion, when the surface of fine particles is to be dendrimer-modified, to prevent coagulation, if bio-derived magnetic bodies are used as fine particles, sufficient dendrimers can be formed easily without causing cracking due to ultrasonic waves.

What is claimed is:

1. A method of extracting nucleic acid or protein using dendrimers, comprising:
    extracting nucleic acid or protein from a fluid using amino radicals of particulate bodies mixed and dispersed in the fluid containing the nucleic acid or protein,
    wherein the particulate bodies comprise multi-layer dendrimers formed on the surface of fine particles, the amino radicals being formed on the surface of the dendrimers.

2. A method of extracting nucleic acid or protein using dendrimers in accordance with claim 1, wherein said fine particles are those of bacteria-derived magnetic bodies, artificial magnetic bodies, metals, plastic beads, glass beads, or gel state substances.

3. A method of extracting nucleic acid or protein using dendrimers in accordance with claim 1 or claim 2, wherein said dendrimers are laminated on the surface of said fine particles after treating the surface of said fine particle with amino-silane.

4. A method of extracting nucleic acid or protein using dendrimers in accordance with claim 1 or claim 2, wherein said dendrimers are of the second generation and above.

5. A method of extracting nucleic acid or protein using dendrimers in accordance with claim 1 or claim 2, wherein protein is extracted using the antigen-antibody reaction by bonding antibodies to the surface of said dendrimers.

6. A fluid containing dendrimers-compositional substances mixed and dispersed in the fluid, wherein the dendrimers-compositional substances are composed of particulate bodies comprising multi-layer dendrimers repeatedly synthesized on the surface of fine particles, and amino radicals covering the surface of the above dendrimers, said particulate bodies being capable of being mixed and dispersed in a fluid containing nucleic acid or protein and configured so that nucleic acid or protein can be captured by these amino radicals.

7. The fluid in accordance with claim 6, wherein said fine particles are those of bacteria-derived magnetic bodies, artificial magnetic bodies, metals, plastic beads, glass beads, or gel state substances.

8. The fluid in accordance with claim 6 or claim 7, wherein said dendrimers are laminated on the surface of said fine particles after treating the surface of said fine particles with amino-silane.

9. The fluid in accordance with claim 6 or claim 7, wherein said dendrimers are of the second generation and above.

10. The fluid in accordance with claim 6 or claim 7, which are configured so that protein is captured using the antigen-antibody reaction by bonding antibodies to the surface of said dendrimers.

11. A method of extracting nucleic acid or protein using dendrimers in which multi-layer dendrimers formed on the surface of fine particles, amino radicals are formed on the surface of the dendrimers, and nucleic acid or protein is extracted using these amino radicals, wherein said fine particles are magnetic bodies.

12. A method of extracting nucleic acid or protein using dendrimers in accordance with claim 11, wherein said magnetic bodies are bacteria-derived magnetic bodies.

13. A method of extracting nucleic acid or protein using dendrimers in accordance with claim 11, wherein said magnetic bodies are artificial magnetic bodies.

14. A method of extracting nucleic acid or protein using dendrimers in accordance with claim 11, wherein said fine particles have a size of about 50 to about 60 microns.

15. A method of extracting nucleic acid or protein using dendrimers in which multi-layer dendrimers formed on the surface of fine particles, amino radicals are formed on the surface of the dendrimers, and nucleic acid or protein is extracted using these amino radicals, wherein said fine particles have a size of about 50 to about 60 microns.

16. Dendrimers-compositional substances which are composed of fine particles, multi-layer dendrimers repeatedly synthesized on the surface of these fine particles, and amino radicals covering the surface of the above dendrimers, and are configured so that nucleic acid or protein can be captured by these amino radicals, wherein said fine particles are magnetic bodies.

17. Dendrimers-compositional substances in accordance with claim 16, wherein said magnetic bodies are bacteria-derived magnetic bodies.

18. Dendrimers-compositional substances in accordance with claim 16, wherein said magnetic bodies are artificial magnetic bodies.

19. Dendrimers-compositional substances in accordance with claim 16, wherein said fine particles have a size of about 50 to about 60 microns.

20. Dendrimers-compositional substances which are composed of fine particles, multi-layer dendrimers repeatedly synthesized on the surface of these fine particles, and amino radicals covering the surface of the above dendrimers, and are configured so that nucleic acid or protein can be captured by these amino radicals, wherein said fine particles have a size of about 50 to about 60 microns.

21. Dendrimers-compositional substances in accordance with claim 20, wherein said fine particles are those of bacteria-derived magnetic bodies, artificial magnetic bodies, metals, plastic beads, glass beads, or gel state substances.

22. A method of extracting nucleic acid or protein using dendrimers in accordance with claim 15, wherein said fine particles are those of bacteria-derived magnetic bodies, artificial magnetic bodies, metals, plastic beads, glass beads, or gel state substances.

23. A method of extracting nucleic acid or protein using dendrimers in accordance with claim 15, wherein the fine particles are dispersed in a fluid containing the nucleic acid or protein.

24. A method of extracting nucleic acid or protein using dendrimers in accordance with claim 11, wherein the fine particles are dispersed in a fluid containing the nucleic acid or protein.

25. The method of claim 1, comprising forming the multi-layers dendrimers on the surface of the fine particles and forming the amino radicals on the surface of the dendrimers.

26. The method of claim 1, wherein the fluid is a solution.

27. The method of claim 23, wherein the fluid is a solution.

28. The method of claim 24, wherein the fluid is a solution.

29. The fluid according to claim 6, which is a solution containing nucleic acid or protein.

* * * * *